United States Patent [19]

Zilm et al.

[11] 4,306,291
[45] Dec. 15, 1981

[54] TREMOR MEASUREMENT DEVICE

[75] Inventors: Duane H. Zilm; Howard L. Kaplan; Dominique M. Durand, all of Toronto, Canada

[73] Assignee: Alcoholism & Drug Addiction Research Foundation, Toronto, Canada

[21] Appl. No.: 103,685

[22] Filed: Dec. 14, 1979

[30] Foreign Application Priority Data

Mar. 27, 1979 [CA] Canada ............................ 324258

[51] Int. Cl.³ .......................................... G06F 15/20
[52] U.S. Cl. .................................. 364/508; 364/421; 128/739; 73/649
[58] Field of Search ............... 364/421, 508; 128/739, 128/733; 73/649

[56] References Cited

U.S. PATENT DOCUMENTS

| 4,010,637 | 3/1977 | Harwell et al. | 364/508 X |
| 4,044,239 | 8/1977 | Shimauchi et al. | 364/508 |
| 4,068,210 | 1/1978 | Corkhill | 364/508 X |
| 4,181,029 | 1/1980 | Talbott, Jr. | 364/508 X |

Primary Examiner—Edward J. Wise
Attorney, Agent, or Firm—Sughrue, Mion, Zinn, Macpeak & Seas

[57] ABSTRACT

Apparatus is provided in which a signal indicative of the tremor is sensed. This signal is amplified in a variable gain amplifier. During an initial time interval the size of the amplifier signal is determined and the gain of the amplifier is adjusted in response to the signal size. Then means are provided for indicating the size of frequency of the adjusted signal during a further time period to give a tremor measurement which may be relatively easily interpreted.

14 Claims, 1 Drawing Figure

TREMOR MEASUREMENT DEVICE

BACKGROUND OF THE INVENTION

This invention relates to apparatus for measuring tremor in a part of a living body, for example in a limb or part of a limb of a human body.

Tremor is a series of involuntary, small variable movements involving a part or parts of the body moved by skeletal muscles. Limb tremor can be divided into two categories, namely normal and abnormal tremor, and these can be sub-divided into rest tremor, postural tremor and intention tremor. Rest tremor occurs when a limb is hanging freely without voluntary movement, and is commonly increased in diseases involving the extrapyramidal system, for example Parkinson's disease. Intention tremor occurs when a limb is voluntarily moved from one position to another, and is increased in diseases where there is a degeneration of the cerebellum and basal ganglia, for example multiple sclerosis, Parkinson's disease and Wilson's disease. Postural or physiologic tremor occurs when a limb is voluntarily maintained in a position rather than rest. Abnormal postural tremor occurs during withdrawal from addiction to alcohol or drugs such as narcotics and barbiturates. Normal postural tremor is increased during fatigue, anxiety and stress. Also, normal postural tremor is reduced by alcohol, and hence may provide an involuntary measure of the effect of alcohol.

For various reasons, some of which will be evident from the proceeding paragraph, the measure of tremor is extremely useful in the treatment of various diseases or other abnormal conditions of the human body. Because of the actual physical movements involved in tremor, i.e. very small rapid movements of widely differing amplitude and frequency, the reliable measurement of tremor and the interpretation of the results of such measurements present considerable problems. To be of practical use, apparatus for the measurement of tremor should not only measure tremor accurately but should also present the results of such measurements in a manner which can be relatively easily interpreted by medical personnel. Known apparatus of this kind has not fulfilled both these requirements.

SUMMARY OF THE INVENTION

It is therefore an object of the invention to provide apparatus for measuring tremor which can not only measure tremor in a sufficiently accurate manner, but which can also indicate the results of such measurements in a manner which can be relatively easily interpreted by medical personnel.

According to the present invention, tremor measuring apparatus includes means for sensing tremor and providing an electrical signal indicative of the tremor, variable gain amplifier means for amplifying the signal, means for sensing the size of the amplified signal during an initial predetermined period of time, means responsive to the signal size sensing means to adjust the variable gain of the amplifier means to a suitable level, and means for determining and indicating the size of frequency of the signal of adjusted amplification during a further predetermined period of time.

Abnormal tremor may be of the order of 100 times greater than normal postural tremor, which in turn may be of the order ten times normal rest tremor. Further, the treatment of abnormal tremor frequently involves a ten to one hundred fold decrease in tremor. Apparatus according to the present invention is capable of effectively measuring such widely different amounts of tremor, and of presenting the results of such measurements in a manner which can be relatively easily interpreted.

Advantageously, the signal size sensing means comprises means for rectifying and integrating the signal, means for resetting the integrating means when the integral of the signal reaches a predetermined level, with the responsive means comprising means for counting the number of times the integral means is reset during the initial predetermined period of time and adjusting the amplifier means accordingly.

The responsive means may include a programmed memory of suitable gain values for the amplifier means corresponding to the number of times the integral means is reset during the initial predetermined period of time, with the responsive means adjusting the amplifier means in accordance with the gain value in the memory corresponding to the number of resets. Thus, the memory can be programmed with gain values as selected in accordance with the results of preliminary experiments with subjects exhibiting various kinds of normal and abnormal tremor.

The indicating means may include means for measuring and squaring the size of the signal of adjusted amplification at intervals during the further predetermined period of time, and means for calculating and indicating the mean of the squared sizes. A knowledge of the mean of the squared sizes, or in other words the variance, is advantageous in the assessment of a medical condition with abnormal tremor as a symptom.

The tremor measuring may also include means for detecting and indicating the dominant frequency of the tremor signal. A knowledge of such frequency is especially useful in assisting the diagnosis and treatment of tremors resulting from diseases of the extra-pyramidal system, such as Parkinson's disease. The frequency detecting means may include means for counting the number of times the tremor signal crosses a zero line during the further predetermined period of time.

For the purposes of this specification it will be understood that the term dominant frequency refers to the most frequently occurring rythmn in the selected period.

BRIEF DESCRIPTION OF THE DRAWINGS

One embodiment of the present invention will now be described, by way of example, with reference to the accompanying drawing, which shows a diagrammatic view of tremor measuring apparatus.

DETAILED DESCRIPTION OF THE INVENTION

Figure 1:
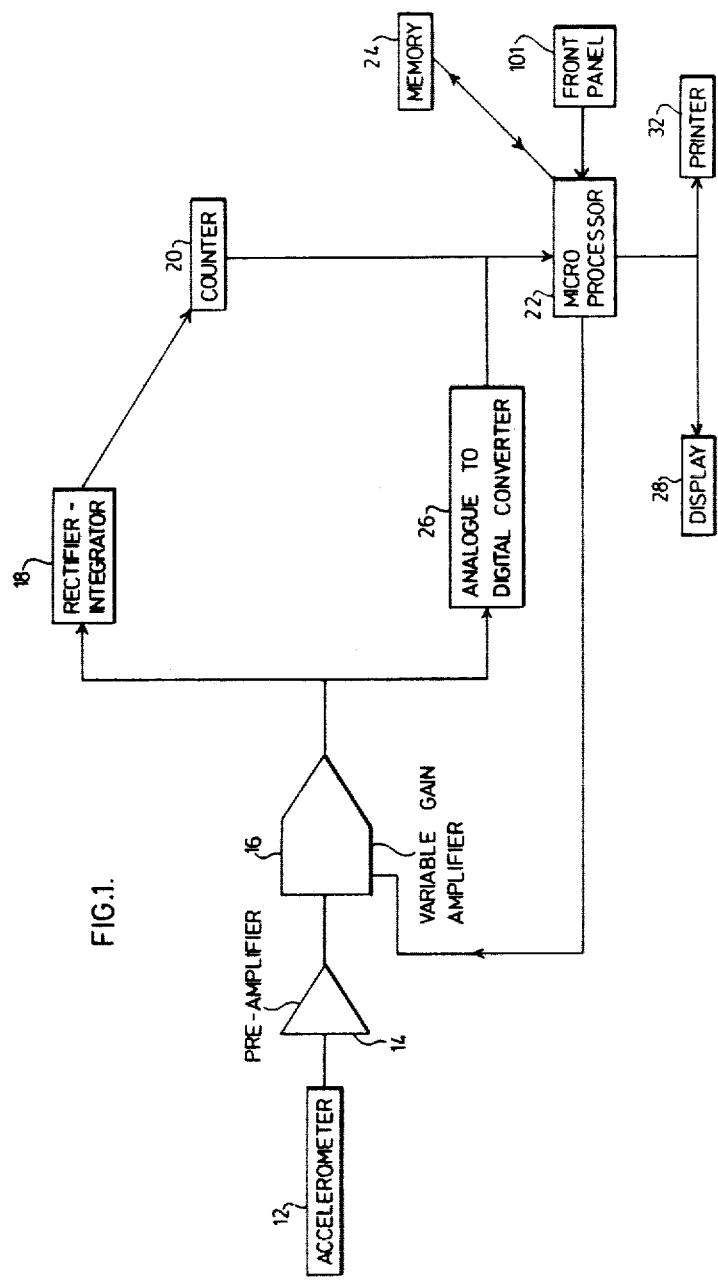

Referring to the drawing, apparatus for measuring tremor in the human hand includes an accelerometer 12 which is secured to the hand to measure postural tremor. Such tremor is preferably measured with the subject sitting comfortably in a chair with the right forearm supported up to the wrist joint at the approximate height of the xiphoid process. The accelerometer 12 is of the piezo-electric type and is secured to the right index finger at the end of the thumb when placed adjacent to the index finger and in such a manner that the most sensitive axis of the accelerometer is in a vertical plane when the hand is in a horizontal plane. Preferably, the fingers of the right hand are taped together to reduce independent motion of the fingers at the metacarpophalangeal joints. With this arrangement, the vertical tremor motion of the hand is measured while the hand is maintained voluntarily and such that the arm muscles are counter-acting torque on the hand about the wrist joint due to the force of gravity acting on the hand. Typical hand tremor frequencies range from about six to ten Hz, and a suitable accelerometer 12 for the purpose of this embodiment is the Bruel and Kjaer Model 4332.

It will of course be understood that other forms of transducers may be substituted for the accelerometer 12 and appropriate changes in circuitry made to compensate for the characteristics of such alternate transducers.

The accelerometer 12 accordingly senses postural tremor in the hand and produces a signal indicative of the tremor. The signal is initially amplified by a pre-amplifier 14, which may advantageously be a high impedance MOSFET amplifer (MOSFET stands for Metal Oxide Semi-conductor Field Effect Transistor). The pre-amplified signal then passes to a variable gain amplifier 16, which is initially set at a gain of one, and initially the amplified signal passes to rectifier-integrator 18, which is associated with a 12-bit binary counter 20. The rectifier-integrator 18 rectifies and integrates the amplified signal and, each time the integral reaches a predetermined level, the integrator 18 is reset to zero. The counter 20 counts the number of times the integrator 18 is reset. Alternatively, if the microprocessor is capable of interrupt processing, the processing unit could be interrupted each time the integrator is reset and the number of interrupts counted by a microprocessor software algorithm.

A programmed processor 22 is arranged to read the number of resets counted by the counter 20 during a predetermined initial period of time of operation of the accelerometer 12. Conveniently, such a predetermined initial period of time is five seconds. A semi-conductor memory 24 associated with the processor 22 contains a suitable table of gain values for the variable gain amplifier 16 corresponding to the number of times the integrator 18 has been reset during the five second period. The processor 22 accordingly acts to adjust the gain of the amplifier 16 to the value contained in the memory 24 according to the number of integrator resets counted by the counter 20 during the five second period. Thus, in this manner, the variable gain amplifier 16 is automatically adjusted to a gain level suitable to ensure that the tremor being measured is amplified to the optimum amount for the best results.

When the gain of the amplifier 16 has been adjusted, the processor 22 directs the signal of adjusted amplification from the amplifier 16 to a 12-bit analogue-to-digital converter 26 for a further period of time which, in this particular embodiment, is 20 seconds. For this period of time, each 12-bit sample of the signal is squared, and the sum is accumulated in memory as a 40-bit number. At the end of the 20 second period, the variance of the signal during this period, that is to say the mean of the squares, is calculated by the processor 22 using an appropriate scale factor taking into account the sensitivity of the accelerometer 12, the gain of the amplifier 16, and the number of 12-bit samples collected over 20 seconds. The variance over the 20 second period is then displayed on a five-digit display 28 in units of $10^{-4}G^2$, where "G"=9.81 m/sec$^2$. If desired, the amplified signal from the amplifier 16 and the actual gain selected for the 20 second period may also be recorded externally using analog recording techniques.

Also during the 20 second period the number of zero crossings of the signal is computed by the processor 22 and that number is used by the processor to compute the signal dominant frequency at the end of the 20 second period. Alternatively, the signal from the amplifier 16 could be passed to a peripheral zero crossing detector which detects the zero crossings of the signal, and the 12-bit counter 20 used to count the number of zero crossings. The processor 22 then could read the counter and calculate the dominant frequency of the signal.

The micro processor 22 also stores the number of times during the 20 second period that the signal has exceeded the input voltage limits of the converter 26, and if a predetermined error threshold in this respect is exceeded, the computation terminates and the display flashes the number 99999 to indicate excessive overflows.

If the measurement is accepted, the variance and frequency are printed out on a printer 32. After a series of measurements, the mean of tremor variances and frequency are computed by the micro processor 22 and printed out on the printer 32.

The front panel 101 has four pushbuttons by which the operator can control the function of the device. "START" initiates a measurement which, provided there are not excessive analogue-to-digital converter overflows or if the operator does not press "STOP", will terminate normally after 25 seconds. "STOP" allows the operator to halt a measurement. The usual recovery is to "START". The instrument can cumulate up to 15 successive measurements. Upon pressing "COMPUTE", the average mean square tremor and frequency are computed, printed, and the memory reset for a new set of averages. "ERASE" allows the operator the option to erase the last tremor measurement from a measurement series. The erasure is indicated on the printer as a row of X's following the values printed for the measurement to be erased.

In one experiment using apparatus according to the above described embodiment, hand tremor was measured in a normal person and in a person suffering from alcohol withdrawal. In each case, five measurements were taken, and the variance and frequency of the measurements was computed and recorded by the apparatus. The variable gain for the 20 second period was also recorded.

With the normal person, the variable gain was from 2000 to 2500, the variance was 5 (in units of $10^{-4}G^2$) and the mean frequency was 9 Hz. With a person with abnormal tremor the variable gain was 10 to 200, the variance was between 50 and 500 and the mean frequency was for Parkinson's Disease 5 Hz, for withdrawal in the range 7 to 9 Hz.

A person skilled in the art will readily understand that the processor 22 also performs various control functions inherent in the function of the apparatus described, for example timing the first and second durations of time, and that the apparatus will also include a manual control for commanding various operations such as start, stop, erase and compute results.

Other embodiments within the scope of the invention will be apparent to a person skilled in the art, the scope of the invention being defined in the appended claims..

The embodiments of the invention in which an exclusive property or privilege is claimed are defined as follows:

1. Apparatus for measuring tremor in a part of a living body, including means for sensing tremor and providing an electrical signal indicative of said tremor, variable gain amplifier means for amplifying said signal, means for sensing the size of said amplified signal during an initial predetermined period of time, means responsive to said signal size sensing means to adjust the variable gain of said amplifier means to a suitable level, and means for determining and indicating the size and frequency of the signal of adjusted amplification during a further predetermined period of time.

2. Tremor measuring apparatus according to claim 1, wherein the signal size sensing means comprises means for rectifying and integrating said signal, means for resetting said integrating means when the integral of said signal reaches a predetermined level, and said responsive means comprises means for counting the number of times the integral means is reset during said initial predetermined period of time and adjusting said amplifier means accordingly.

3. Tremor measuring apparatus according to claim 2, wherein said responsive means includes a programmed memory of suitable gain values for said amplifier means corresponding to the number of times the integral means is reset during said initial predetermined period of time, and said responsive means adjusts said amplifier means in accordance with the gain value in said memory corresponding to said number of resets.

4. Apparatus as claimed in claim 2 further including means for determining and indicating the mean of the mean square signal size and mean of the signal frequencies of a plurality of predetermined periods.

5. Tremor measuring apparatus according to claim 1, wherein said indicating means includes means for measuring and squaring the size of said signal of adjusted amplification at intervals during said further predetermined period of time, and means for calculating and indicating the mean squared sizes.

6. Apparatus as claimed in claim 5 further including means for determining and indicating the mean of the mean square signal size and mean of the signal frequencies of a plurality of predetermined periods.

7. Tremor measuring apparatus according to claim 1, further including means for detecting and indicating the dominant frequency of the tremor signal.

8. Tremor measuring apparatus according to claim 7, wherein said frequency detecting means includes means for counting the number of times the tremor signal crosses a zero line during said further predetermined period of time.

9. Apparatus as claimed in claim 7 further including means for determining and indicating the mean of the mean square signal size and mean of the signal frequencies of a plurality of predetermined periods.

10. Tremor measuring apparatus according to claim 1, wherein said tremor sensing means comprises an accelerometer.

11. Apparatus as claimed in claim 10 further including means for determining and indicating the mean of the mean square signal size and means of the signal frequencies of a plurality of predetermined periods.

12. Tremor measuring apparatus according to claim 1, wherein the signal size sensing means comprises means for rectifying and integrating said signal, means for resetting said integrating means when the integral of said signal reaches its predetermined level, said responsive means comprises means for counting the number of times the integral means is reset during said initial predetermined period of time and adjusting said amplifier means accordingly, and said indicating means includes means for measuring and squaring the size of said signal of adjusted amplification at intervals during said further predetermined period of time, and means for calculating and indicating the mean of the squared sizes.

13. Apparatus as claimed in claim 12 further including means for determining and indicating the mean of the mean square signal size and mean of the signal frequencies of a plurality of predetermined periods.

14. An apparatus as claimed in claim 1 further including means for determining and indicating the mean of the mean square signal size and mean of the signal frequencies of a plurality of predetermined periods.

* * * * *